United States Patent
Pollard

(10) Patent No.: US 8,716,235 B2
(45) Date of Patent: May 6, 2014

(54) METHOD FOR INHIBITING METASTASIS BY USING ANTI-CCL3 ANTIBODIES

(71) Applicant: Albert Einstein College of Medicine of Yeshiva University, Bronx, NY (US)

(72) Inventor: Jeffrey W. Pollard, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/860,109

(22) Filed: Apr. 10, 2013

(65) Prior Publication Data

US 2013/0280254 A1     Oct. 24, 2013

Related U.S. Application Data

(60) Provisional application No. 61/625,787, filed on Apr. 18, 2012.

(51) Int. Cl.
*A61K 38/00* (2006.01)
*A61P 35/04* (2006.01)
*A61K 39/395* (2006.01)

(52) U.S. Cl.
USPC ..... 514/19.8; 514/19.3; 514/19.5; 424/130.1; 424/133.1

(58) Field of Classification Search
CPC combination set(s) only.
See application file for complete search history.

(56) References Cited

U.S. PATENT DOCUMENTS 6,974,817 B2 * 12/2005 Hayward ................. 514/253.01
2009/0298845 A1    12/2009 Carter et al.

OTHER PUBLICATIONS

Qian B Z et al., entitled "CCL3 autocrine signaling regulate retention of metastasis associated macrophages and promote breast cancer metastasis," AACR Annual Meeting, Apr. 2, 2012, Abstract.

* cited by examiner

*Primary Examiner* — Elly-Gerald Stoica
(74) *Attorney, Agent, or Firm* — Amster, Rothstein & Ebenstein LLP

(57) ABSTRACT

Methods and compositions are provided for inhibiting metastasis of a tumor in a subject, or of inhibiting progression of a primary tumor in a subject which requires macrophages for progression.

7 Claims, 10 Drawing Sheets

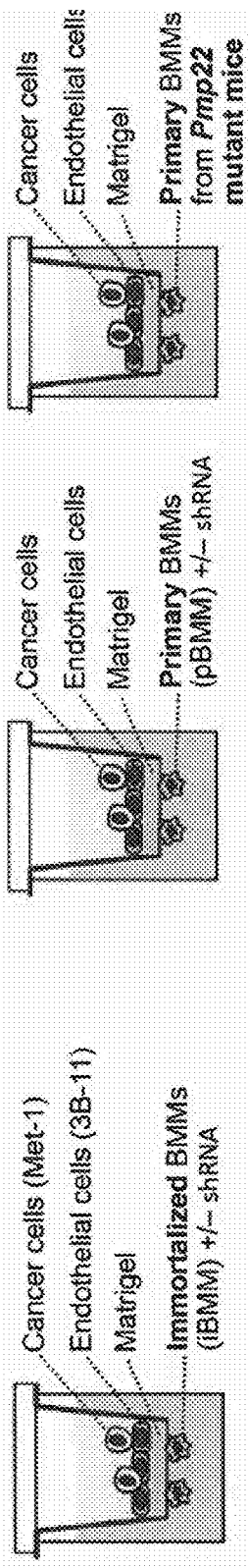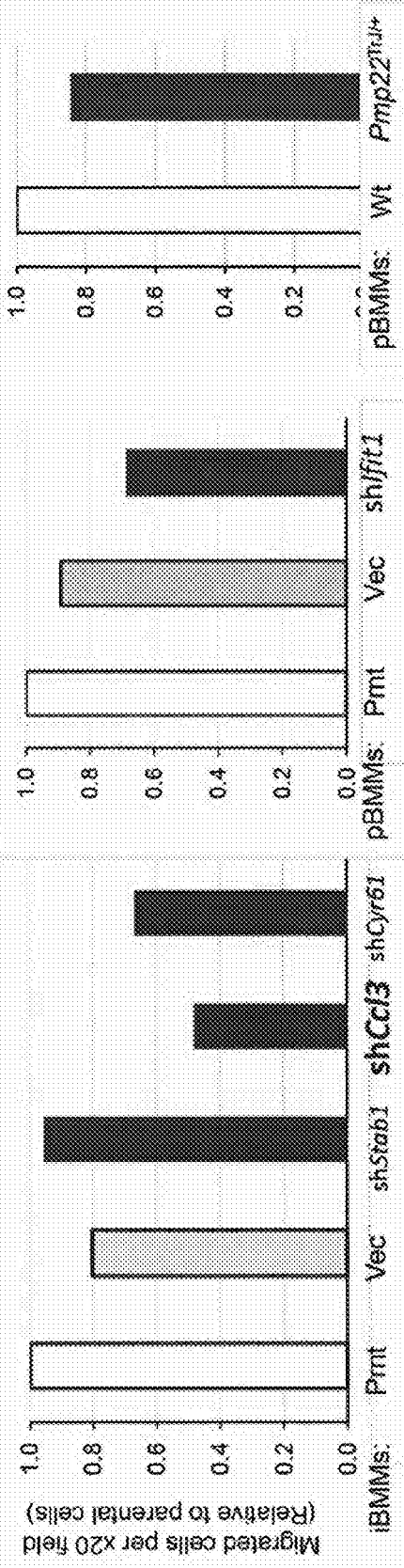
Fig. 3
3rd screening: Genes suppressed in MΦ that lacks CCR2
*In vitro extravasation assay*

US 8,716,235 B2

METHOD FOR INHIBITING METASTASIS BY USING ANTI-CCL3 ANTIBODIES

CROSS-REFERENCE TO RELATED APPLICATIONS

This application claims benefit of U.S. Provisional Application No. 61/625,787, filed Apr. 18, 2012, the contents of which are hereby incorporated by reference.

STATEMENT OF GOVERNMENT SUPPORT

This invention was made with government support under grant number P01 CA 100324 awarded by the National Institutes of Health. The government has certain rights in the invention.

BACKGROUND OF THE INVENTION

Throughout this application various publications, books, patents and patent application publications are referred to. The disclosures of all of these are hereby incorporated by reference in their entireties into the subject application to more fully describe the art to which the subject application pertains.

Metastasis is a prevalent killer. There are no established effective anti-metastatic therapeutics. Macrophages promote tumor progression and metastasis, and act at both the primary and secondary tumor site. At the metastatic sites, a sub-population of macrophages called metastasis associated macrophages (MAMs) is recruited by chemoattractant CCLs (Chemokine (C-C motif) ligands) largely produced by tumor cells and acting through the macrophage expressed receptor, CCR2 (C-C chemokine receptor type 2). Therapeutics aimed at all macrophages have moved into clinical trials, but these lack targeting specificity and so have toxicity issues. Targeting specific molecules synthesized by monocytes and macrophages at the tumor site is preferred.

The present invention addresses the need for novel and specific treatments for inhibiting metastasis.

SUMMARY OF THE INVENTION

A method is provided of inhibiting metastasis of a tumor in a subject, or of inhibiting progression in a subject of a primary tumor which requires macrophages for progression, comprising administering to the subject an amount of an inhibitor of CCL3 (Chemokine (C-C motif) ligand 3) effective to inhibit metastasis of a tumor or inhibit progression of a primary tumor requiring macrophages for progression.

Also provided is a method of inhibiting metastasis of a tumor in a subject, or of inhibiting progression in a subject, of a primary tumor which requires macrophages for progression, comprising administering to the subject an amount of an antagonist of a CCR5 receptor (Chemokine (C-C motif) receptor type 5) or of an antagonist of a CCR1 receptor (Chemokine (C-C motif) receptor type 1) effective to inhibit metastasis of a tumor or inhibit progression of a primary tumor requiring macrophages for progression.

Also provided is a method for identifying an agent as a candidate inhibitor of metastasis, the method comprising: contacting a preparation comprising the macrophage and CCL3 in the absence of the agent and under conditions permitting the CCL3 to activate the macrophage, and determining CCL3 activation of the macrophage, contacting a preparation comprising a macrophage and CCL3 under the conditions, and in the presence of the agent, and determining CCL3 activation of the macrophage,
wherein a reduction in activation of the macrophage in the presence of the agent as compared to in the absence of the agent indicates that the agent is a candidate inhibitor of metastasis, and wherein no change in or an increase in activation of the macrophage in the presence of the agent as compared to in the absence of the agent does not indicate that the agent is a candidate inhibitor of metastasis.

Also provided is a method for identifying an agent as a candidate inhibitor of progression of a primary tumor requiring macrophages for progression, the method comprising: contacting a preparation comprising a macrophage and CCL3 in the absence of the agent and under conditions permitting the CCL3 to activate the macrophage, and determining CCL3 activation of the macrophage,
contacting a preparation comprising the macrophage and CCL3 under the conditions, and in the presence of the agent, and determining CCL3 activation of the macrophage,
wherein a reduction in activation of the macrophage in the presence of the agent as compared to in the absence of the agent indicates that the agent is a candidate inhibitor of progression of a primary tumor requiring macrophages for progression, and wherein no change in or an increase in activation of the macrophage in the presence of the agent as compared to in the absence of the agent does not indicate that the agent is a candidate inhibitor of progression of a primary tumor requiring macrophages for progression.

BRIEF DESCRIPTION OF THE FIGURES

FIG. 3. Screening assay showing that CCL3 has an effect in promotion of tumor cell extravasation.

DETAILED DESCRIPTION OF THE INVENTION

Figure 1:
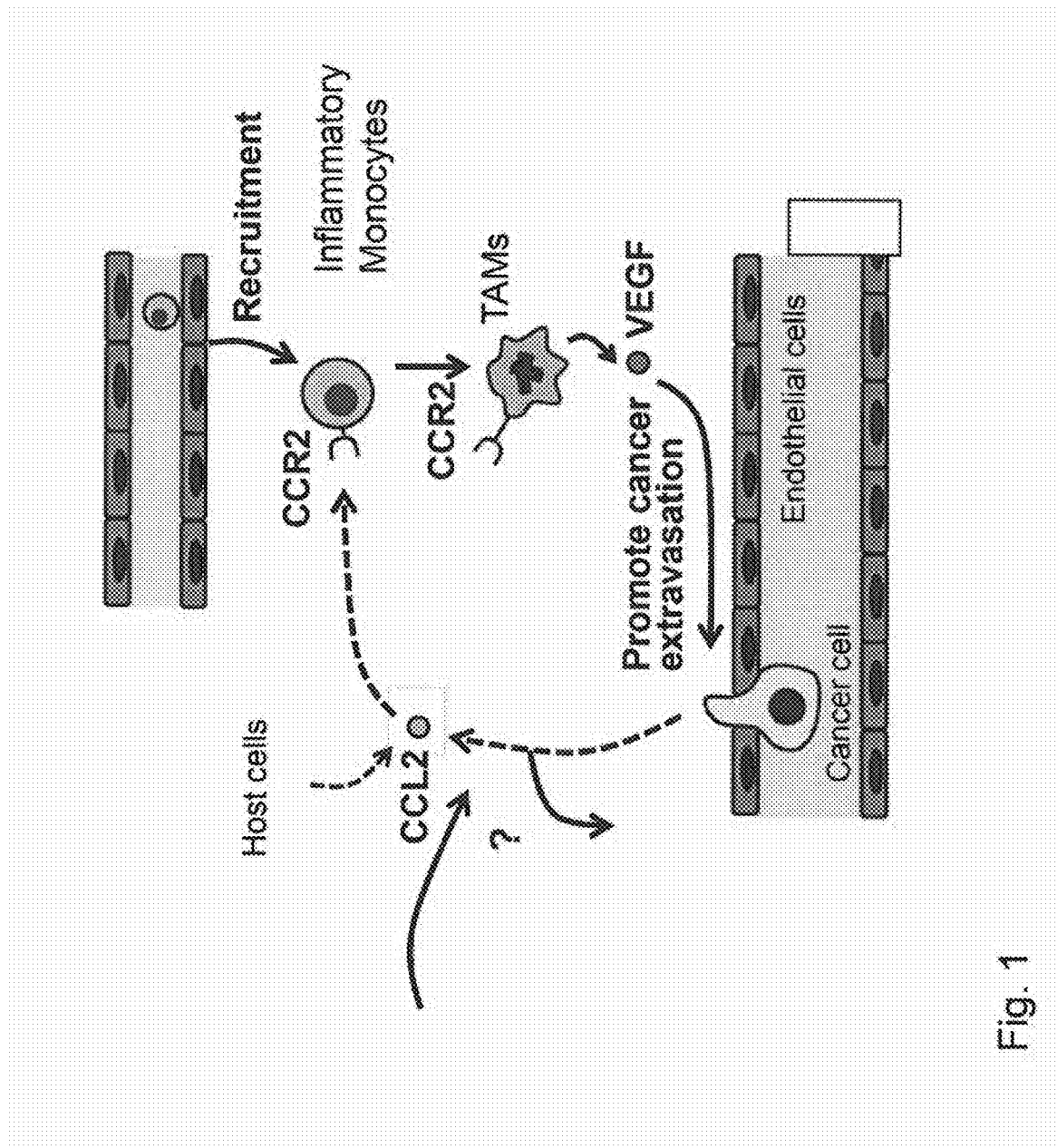
FIG. 1. Schematic of how CCL2 recruits inflammatory monocytes to the site of metastatic cell extravasation. These monocytes and their differentiated progeny, metastasis associated macrophages (MAMs), promote tumor cell seeding and persistent growth.

A method is provided of inhibiting metastasis of a tumor in a subject, or of inhibiting progression in a subject of a primary tumor which requires macrophages for progression, comprising administering to the subject an amount of an inhibitor of CCL3 effective to inhibit metastasis of a tumor or inhibit progression of a primary tumor requiring macrophages for progression. In an embodiment, the method is of inhibiting metastasis of a tumor in a subject. In an embodiment, the method is of inhibiting progression in a subject of a primary tumor which requires macrophages for progression.

Also provided is a method of inhibiting metastasis of a tumor in a subject, or of inhibiting progression in a subject, of a primary tumor which requires macrophages for progression, comprising administering to the subject an amount of an antagonist of a CCR5 receptor or of an antagonist of a CCR1 receptor effective to inhibit metastasis of a tumor or inhibit progression of a primary tumor requiring macrophages for progression. In an embodiment, the method is of inhibiting metastasis of a tumor in a subject comprising administering to the subject an amount of an antagonist of a CCR5 receptor. In an embodiment, the method is of inhibiting progression in a subject of a primary tumor which requires macrophages for progression comprising administering to the subject an amount of an antagonist of a CCR5 receptor. In an embodiment, the method is of inhibiting metastasis of a tumor in a subject comprising administering to the subject an amount of an antagonist of a CCR1 receptor. In an embodiment, the method is of inhibiting progression in a subject of a primary tumor which requires macrophages for progression comprising administering to the subject an amount of an antagonist of a CCR1 receptor.

In an embodiment of the methods, the tumor is a tumor of the breast, nasopharynx, pharynx, lung, bone, brain, sialaden, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid or skin or is a glioma. In an embodiment of the methods, the tumor is a tumor of the breast, endometrium or prostate or wherein the primary tumor is a brain tumor or glioma. In an embodiment of the methods, metastasis is inhibited in lung, bone and/or brain tissue.

In an embodiment of the methods, the inhibitor of CCL3 is an antibody, a fragment of an antibody, a small organic molecule of less than 2000 daltons, or comprises a siRNA or shRNA. In an embodiment of the methods, the inhibitor of CCL3 is an antibody or fragment of an antibody. In an embodiment of the methods, the antibody is a human antibody, a humanized antibody or a chimeric antibody or wherein the fragment is of a human antibody, of a humanized antibody or of a chimeric antibody. In an embodiment of the methods, the antibody is a monoclonal antibody or the fragment is of a monoclonal antibody. In an embodiment of the methods, the fragment comprises an Fab, an Fab', an $F(ab')_2$, an $F_d$, an $F_v$, a complementarity determining region (CDR), or a single-chain antibody (scFv).

In an embodiment of the methods, the CCL3 is metastasis-associated-macrophage-secreted CCL3. In an embodiment, the methods further comprise administering to the subject an amount of an antagonist of a CCR5 receptor or an antagonist of a CCR1 receptor.

In an embodiment of the methods, the CCR5 receptor and/or CCR1 receptor is on a metastasis-associated-macrophage. In an embodiment of the methods, the CCR5 receptor antagonist and/or CCR1 receptor antagonist is an antibody, a fragment of an antibody, a small organic molecule of less than 2000 daltons, or comprises a siRNA or shRNA. In an embodiment of the methods, the CCR5 receptor antagonist and/or CCR1 receptor antagonist is an antibody or fragment of an antibody. In an embodiment of the methods, the antibody is a human antibody, a humanized antibody or a chimeric antibody or wherein the fragment is of a human antibody, of a humanized antibody or of a chimeric antibody. In an embodiment of the methods, the antibody is a monoclonal antibody or the fragment is of a monoclonal antibody. In an embodiment of the methods, the fragment comprises an Fab, an Fab', an $F(ab')_2$, an $F_d$, an $F_v$, a complementarity determining region (CDR), or a single-chain antibody (scFv). In an embodiment of the methods, both a CCR5 antagonist and a CCR1 antagonist are administered. In an embodiment, the methods further comprise administering to the subject an amount of an inhibitor of CCL3.

Also provided is a method for identifying an agent as a candidate inhibitor of metastasis, the method comprising:
contacting a preparation comprising the macrophage and CCL3 in the absence of the agent and under conditions permitting the CCL3 to activate the macrophage, and determining CCL3 activation of the macrophage,
contacting a preparation comprising a macrophage and CCL3 under the conditions, and in the presence of the agent, and determining CCL3 activation of the macrophage,
wherein a reduction in activation of the macrophage in the presence of the agent as compared to in the absence of the agent indicates that the agent is a candidate inhibitor of metastasis, and wherein no change in or an increase in activation of the macrophage in the presence of the agent as compared to in the absence of the agent does not indicate that the agent is a candidate inhibitor of metastasis. In an embodiment, determining activation comprises quantifying activation. In an embodiment, determining comprises experimentally determining. The method can comprise the step of identifying the agent as a candidate inhibitor of metastasis.

Also provided is a method for identifying an agent as a candidate inhibitor of progression of a primary tumor requiring macrophages for progression, the method comprising:
contacting a preparation comprising a macrophage and CCL3 in the absence of the agent and under conditions permitting the CCL3 to activate the macrophage, and determining CCL3 activation of the macrophage,
contacting a preparation comprising the macrophage and CCL3 under the conditions, and in the presence of the agent, and determining CCL3 activation of the macrophage,
wherein a reduction in activation of the macrophage in the presence of the agent as compared to in the absence of the agent indicates that the agent is a candidate inhibitor of progression of a primary tumor requiring macrophages for progression, and wherein no change in or an increase in activation of the macrophage in the presence of the agent as compared to in the absence of the agent does not indicate that the agent is a candidate inhibitor of progression of a primary tumor requiring macrophages for progression. In an embodiment, determining activation comprises quantifying activation. In an embodiment, determining comprises experimentally determining. The method can comprise the step of identifying the agent as a candidate inhibitor of progression of a primary tumor requiring macrophages for progression.

In an embodiment of the methods, the macrophage is a macrophage bearing a CCR5 receptor and/or a CCR1 receptor. In an embodiment of the methods, the agent is an antibody, a fragment of an antibody, a small organic molecule of less than 2000 daltons, or comprises a siRNA or shRNA. In an embodiment of the methods, the agent is an antibody and is a human antibody, a humanized antibody or a chimeric antibody or wherein the fragment is of a human antibody, of a humanized antibody or of a chimeric antibody. In an embodiment of the methods, the agent is an antibody fragment and comprises an Fab, an Fab', an $F(ab')_2$, an $F_d$, an $F_v$, a complementarity determining region (CDR), or a single-chain antibody (scFv). In an embodiment of the methods, the agent is an antibody fragment and comprises an Fab, an Fab', an F(ab')$_2$, an F$_d$, an F$_v$, a complementarity determining region (CDR), or a single-chain antibody (scFv). In an embodiment of the methods, the antibody or antibody fragment is an anti-CCL3 antibody or fragment of an anti-CCL3 antibody. In an embodiment of the methods, the antibody or antibody fragment is an anti-CCR1 receptor antibody or fragment of an anti-CCR1 receptor antibody, or anti-CCR5 receptor antibody or fragment of an anti-CCR5 receptor antibody.

As used herein, "inhibiting metastasis of a tumor in a subject" means that one or more symptoms or one or more other parameters by which the disease is characterized, are reduced, ameliorated, prevented, placed in a state of remission, or maintained in a state of remission. Non-limiting examples of such parameters include uncontrolled degradation of the basement membrane and proximal extracellular matrix, and travel of tumor cells through the bloodstream or lymphatics, invasion, dysregulated adhesion, and proliferation at a secondary site. In an embodiment, the metastasis inhibited is metastasis of a primary tumor.

As used herein, "inhibiting progression in a subject of a primary tumor" means that one or more symptoms of the disease, such as the primary tumor itself, vascularization of the primary tumor, or other parameters by which the disease is characterized, are reduced, ameliorated, prevented, placed in a state of remission, or maintained in a state of remission. "Treating" a primary tumor also means that one or more hallmarks of the primary tumor may be eliminated, reduced or prevented by the treatment. Non-limiting examples of such hallmarks include migration, division, and organization of the endothelial cells into new functioning capillaries, and the persistence of such functioning capillaries, and/or of tumor mass and/or invasion.

As used herein, "a primary tumor which requires macrophages for progression" means a solid tumor such as a brain tumor, a glioma, or a breast, fibrosarcoma, pancreatic or neuroendocrine tumor. Such tumors requiring macrophages for progression are known in the art.

As used herein, the term "antibody" refers to an intact antibody, i.e. with complete Fc and Fv regions. "Fragment" refers to any portion of an antibody, or portions of an antibody linked together, such as, in non-limiting examples, a Fab, F(ab)$_2$, a single-chain Fv (scFv), which is less than the whole antibody but which is an antigen-binding portion and which competes with the intact antibody of which it is a fragment for specific binding. As such a fragment can be prepared, for example, by cleaving an intact antibody or by recombinant means (scFv). See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer CCL3-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an F$_d$ fragment means an antibody fragment that consists of the V$_H$ and CH1 domains; an F$_v$ fragment consists of the V$_L$ and V$_H$ domains of a single arm of an antibody; and a dAb fragment (Ward et al., Nature 341: 544-546 (1989) hereby incorporated by reference in its entirety) consists of a V$_H$ domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" is not intended, unless otherwise indicated, to be limited as regards to the source of the antibody or the manner in which it is made (e.g., by hybridoma, phage selection, recombinant expression, transgenic animals, etc.). The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target CCL3, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g. by appropriate recombinant means once the sequence thereof is identified.

The invention provides isolated antibodies directed against metastasis-associated macrophage-secreted mammalian CCL3. As used herein, the terms "isolated antibody" refers to an antibody that by virtue of its origin or source of derivation has one to four of the following:

(1) is not associated with naturally associated components that accompany it in its native state, (2) is free of other proteins from the same species, (3) is expressed by a cell from a different species, or (4) does not occur in nature.

In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC.

As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, J. Mol. Biol., 227: 381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147(1): 86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen (e.g. CCL3) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. Veloclmmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences identical to those of human origin, but excluding antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", which the invention disclosed herein encompasses directed at CCL3, as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

"Humanized" forms of non-human (e.g., murine) antibodies as encompassed by the present invention are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321: 522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the antibody or antibody fragment of the invention specifically binds to or preferentially binds to the CCL3.

As used herein, the terms "is capable of specifically binding", "specifically binds", or "preferentially binds" refers to the property of an antibody or fragment of binding to the (specified) antigen with a dissociation constant that is <1 µM, preferably <1 nM and most preferably <10 pM. In an embodiment, the Kd of the antibody for CCL3 is 250-500 pM. An epitope that "specifically binds", or "preferentially binds" (used interchangeably herein) to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CCL3 conformational epitope is an antibody that binds this epitope with greater affinity, avidity, more readily, and/or with greater duration than it binds to other CCL3 epitopes or non-CCL3 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

In an embodiment the antibody or fragment neutralizes CCL3 when bound thereto.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the $V_H$ (H1, H2, H3) and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

The disclosures herein regarding antibodies and antibody fragments also apply to CCR5 and CCR1, mutatis mutandis, in regard to methods disclosed herein where a CCR5 receptor antagonist, or an antagonist of a CCR1 receptor, is employed and the antagonist is an antibody.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5 -bis(2-hydroxyethoxy)oxolan-2-yl]-2-(2-hydroxyethoxy)ethoxy]ethyl(E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Kd", as used herein, is intended to refer to the dissociation constant of an antibody-antigen interaction. One way of determining the Kd or binding affinity of antibodies to CCL3 is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of an anti-CCL3 Fab fragment of an antibody can be determined by surface plasmon resonance (BIAcore3000™ surface plasmon resonance (SPR) system, BlAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. CCL3 can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated Kd) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant (Kd) values are calculated as $k_{off}/k_{on}$. This protocol is suitable for use in determining binding affinity of an antibody or fragment to any CCL3. Other protocols known in the art may also be used. For example, ELISA of CCL3 with mAb can be used to determine the kD values. The Kd values reported herein used this ELISA-based protocol.

In an embodiment, the CCL3 is inhibited through RNAi, for example by administering an siRNA or an shRNA. An siRNA (small interfering RNA) as used in the methods or compositions described herein comprises a portion which is complementary to an mRNA sequence encoding a mammalian CCL3, e.g. in a non-limiting example, NCBI Reference Sequence: NM_002983.2, and the siRNA is effective to inhibit expression of mammalian CCL3. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding mammalian CCL3. In another embodiment, a siRNA of the invention comprises a double-stranded RNA wherein one strand of the RNA comprises a portion having a sequence the same as a portion of 18-25 consecutive nucleotides of an RNA transcript of a gene encoding mammalian CCL3. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In an embodiment, the CCR5 and/or CCR1 is inhibited through RNAi, for example by administering an siRNA or an shRNA. An siRNA (small interfering RNA) as used in the methods or compositions described herein comprises a portion which is complementary to an mRNA sequence encoding a mammalian CCR5 or CCR1, e.g. in a non-limiting example, encoding sequence GenBank AAB57793.1, or a sequence encoding NCBI Reference Sequence NP_001286.1, and the siRNA is effective to inhibit expression of mammalian CCR5 or CCR1, respectively. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding mammalian CCR5 or CCR1. In another embodiment, a siRNA of the invention comprises a double-stranded RNA wherein one strand of the RNA comprises a portion having a sequence the same as a portion of 18-25 consecutive nucleotides of an RNA transcript of a gene encoding mammalian CCR5 or CCR1. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length. In yet another embodiment, a siRNA of the invention is 46 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In one embodiment, RNAi inhibition of CCL3 is effected by a short hairpin RNA ("shRNA"). The shRNA can be introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, or mRNA, encoding CCL3. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

In an embodiment of the methods and of the compositions herein, the mammalian CCL3 is a human CCL3. (CCL3 is the chemokine (C—C motif) ligand 3).

In an embodiment, the CCL3 comprises the sequence, or has 90% or greater, or 95% or greater, identity to the sequence: MQVSTAALAV LLCTMALCNQ FSAS- LAADTP TACCFSYTSR QIPQNFIADY FETSSQCSKP GVIFLTKRSR QVCADPSEEW VQKYVSDLEL SA (SEQ ID NO:1). In an embodiment, the CCL3 is encoded by a nucleic acid having the sequence NCBI Reference Sequence: NG_023325.1 or NCBI Reference Sequence: NM_002983.2.

In one embodiment, RNAi inhibition of CCR5 or CCR1 is effected by a short hairpin RNA ("shRNA"). The shRNA can be introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, or mRNA, encoding CCR5 or the target gene, or mRNA, encoding CCR1. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

CCR5 is C—C chemokine receptor type 5. CCR1 is C—C chemokine receptor type 1. In an embodiment, the CCR5 is a human CCR5 and the antagonist thereto blocks or reduces the activity of the human CCR5. In an embodiment, the CCR1 is a human CCR1 and the antagonist thereto blocks or reduces the activity of the human CCR1.

In an embodiment, the CCR1 comprises the following sequence:

```
                                                          (SEQ ID NO: 2)
  1 METPNTTEDY DTTTEFDYGD ATPCQKVNER AFGAQLLPPL YSLVFVIGLV GNILVVLVLV

61 QYKRLKNMTS IYLLNLAISD LLFLFTLPFW IDYKLKDDWV FGDAMCKILS GFYYTGLYSE

121 IFFIILLTID RYLAIVHAVF ALRARTVTFG VITSIIIWAL AILASMPGLY FSKTQWEFTH

181 HTCSLHFPHE SLREWKLFQA LKLNLFGLVL PLLVMIICYT GIIKILLRRP NEKKSKAVRL

241 IFVIMIIFFL FWTPYNLTIL ISVFQDFLFT HECEQSRHLD LAVQVTEVIA YTHCCVNPVI

301 YAFVGERFRK YLRQLFHRRV AVHLVKWLPF LSVDRLERVS STSPSTGEHE LSAGF
```

As used herein a "small molecule" is an organic compound which contains carbon-carbon bonds, and has a molecular weight of less than 2000. The small molecule may be a substituted hydrocarbon or an substituted hydrocarbon. In an embodiment, the small molecule has a molecular weight of less than 1500. In an embodiment, the small molecule has a molecular weight of less than 1000. In an embodiment, the small molecule has a molecular weight of less than 500.

A "candidate inhibitor" is an agent identified by the methods disclosed and can be considered as a lead agent based on its observed activity. A candidate agent may itself be administered in the methods of treatment or maybe used as a basis for a derivative agent.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Transciptome profiling of the MAMs, in comparison with resident lung and spleen macrophages, revealed enrichment of many transcripts suggesting these are important downstream mediators of MAM function. As ablation of MAMs dramatically inhibited metastatic tumor cell seeding and subsequent growth, these downstream genes acted as potential targets to specifically inhibit metastasis. The data disclosed herein shows that CCR2 not only acts as a chemoattractive receptor but also as a signaling receptor altering the differentiation of the recruited monocytes into the MAMS. Thus many transcripts among those enriched in MAMs are regulated directly by CCR2 signaling. Among these is the chemokine CCL3 (formerly known as monocyte inhibitory factor 1 alpha). The experimental evidence herein shows this chemokine is required to reinforce the recruitment of monocytes to the extravasating tumor cells and also to the subsequent metastatic lesions. This is through the receptors CCR1 and CCR5 expressed on MAMs. It is disclosed herein that inhibition of CCL3 action using either antibodies or genetic ablation inhibited metastasis.

Tumor-(and host-) derived CCL2 promotes cancer extravasation through recruitment of inflammatory monocytes that are origin of tumor associated macrophages TAMs (FIG. 1). CCL2 recruits inflammatory monocytes to the site of metastatic cell extravasation. These monocytes and their differentiated progeny, metastasis associated macrophages (MAMs), promote tumor cell seeding and persistent growth. CCL2 promotes recruitment of inflammatory monocytes to the metastasizing sites (e.g. lung) The inflammatory monocytes are the origin of TAMs, and TAMs promote extravasation of cancer cells (TAMs enhance vascular permeability though secretion of VEGF). Herein, the molecular mechanism(s) by which macrophages promote metastasis of breast cancer cells through activation of CCR2 signaling was investigated.

Figure 2:
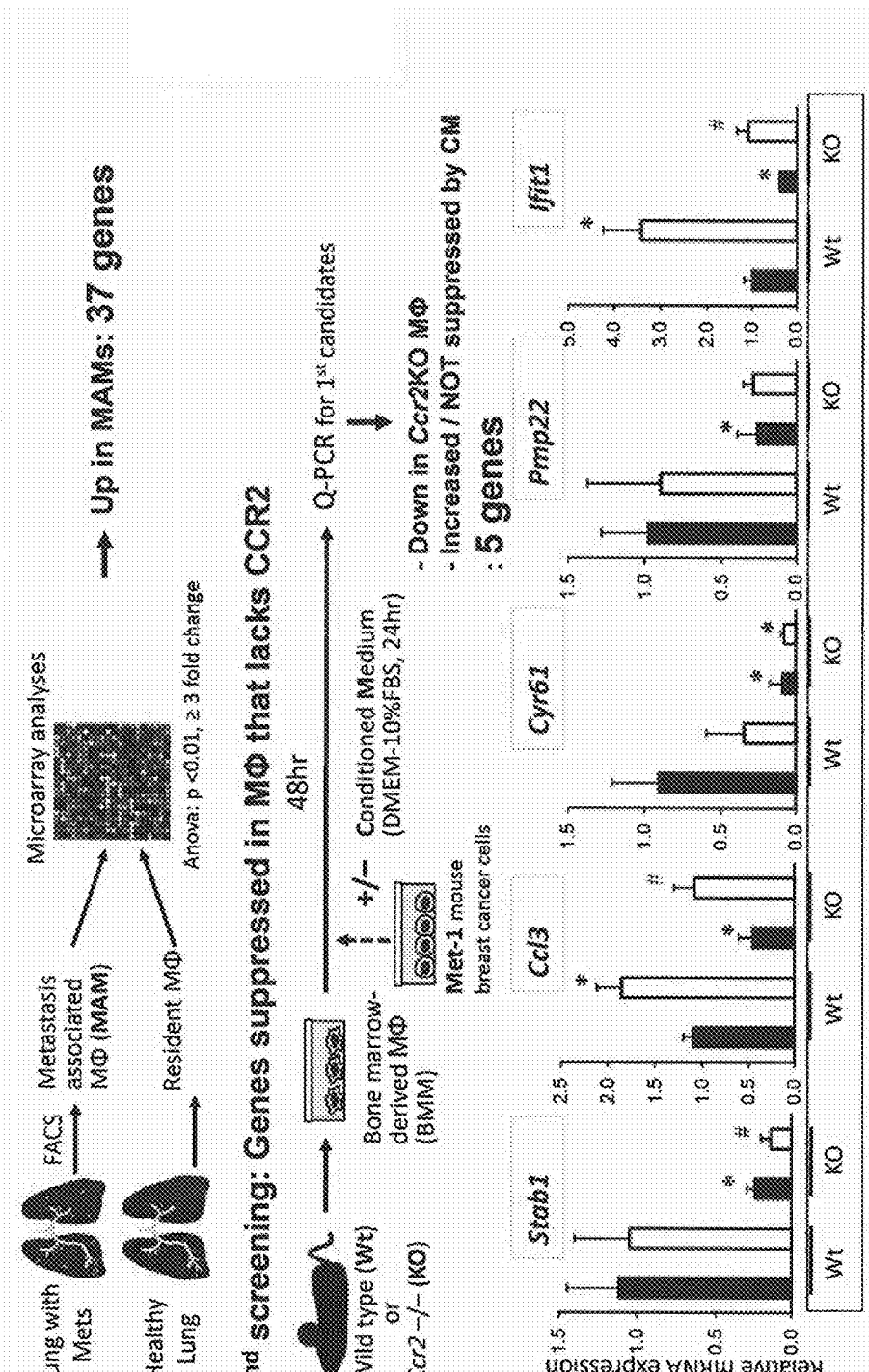
FIG. 2. Strategy for defining genes regulated by CCL2.
Figure 4:
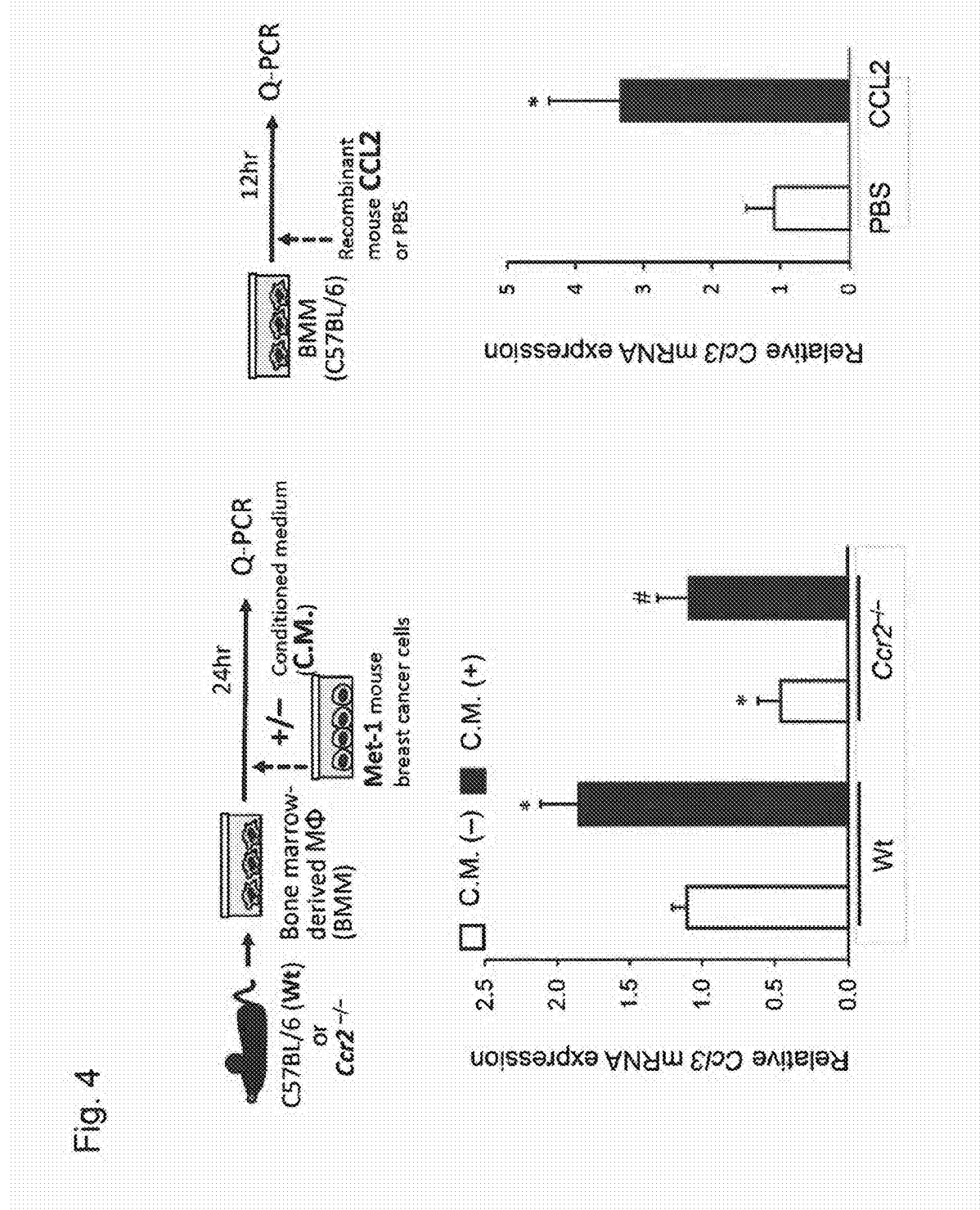
FIG. 4. CCL3 is regulated by CCR2 in macrophages.
Figure 5:
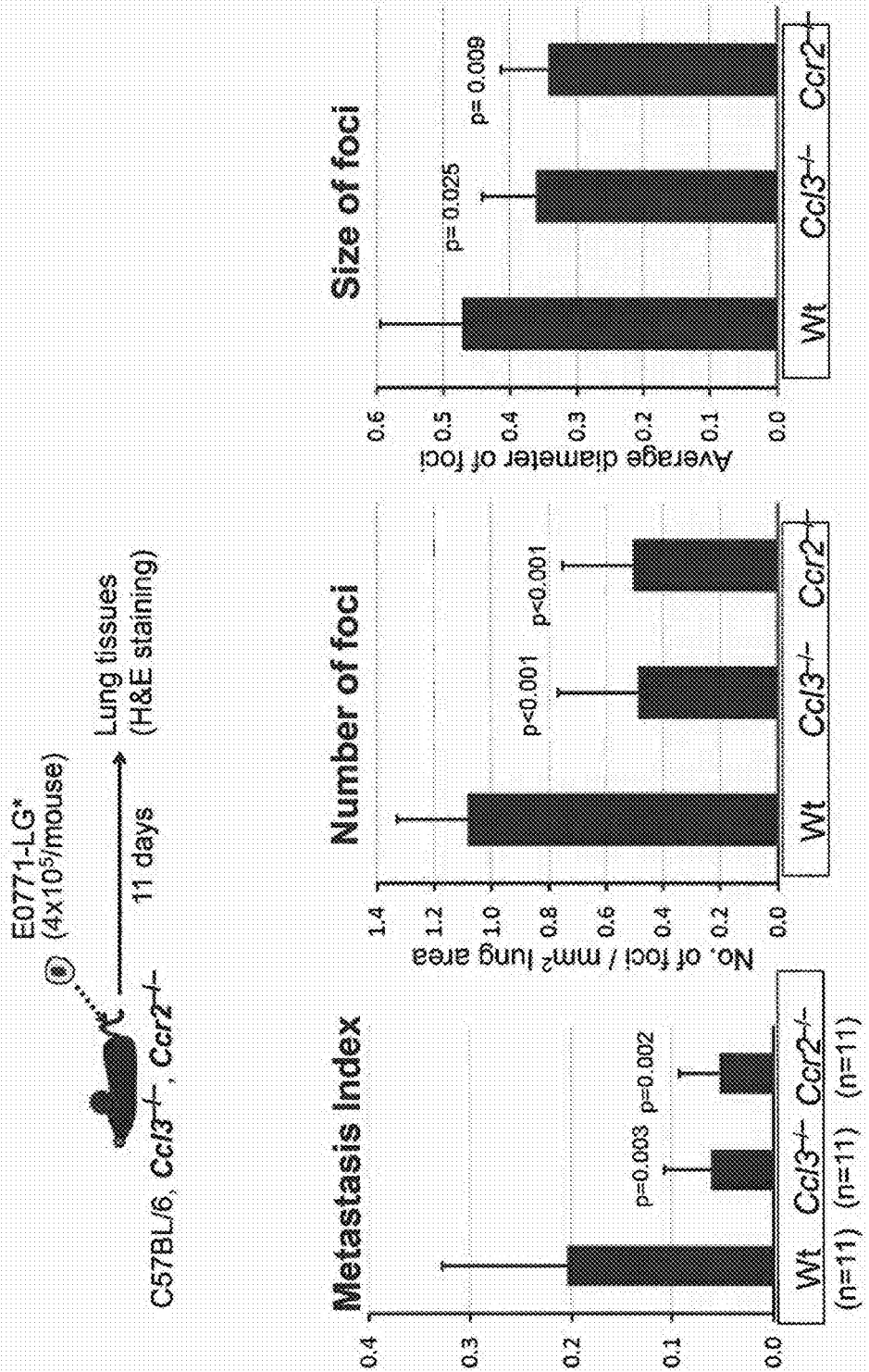
FIG. 5. Metastasis assay in mice homozygous for null mutations in CCL3 and CCL2 genes. Loss of CCL3 reduced the metastatic seeding and growth.

Firstly, genes that are upregulated in metastasis associated MΦ (MAM) were screened (FIG. 2). Then genes suppressed in MΦ that lack CCR2 were screened (FIG. 3). Of the identified genes, CCL3 was focused upon as it is a secreted molecule involved in macrophage biology regulated by CCL2. In an in vitro extravasation assay it was observed that CCL3 has an effect in promotion of tumor cell extravasation. CCL3 is regulated by CCR2 in macrophages as shown by CCR2 activation increasing CCL3 mRNA expression in cultured macrophages (FIG. 4). It was then observed that lack of CCL3 or CCR2 reduces number of lung metastasis foci developed by E0771-LG cells (a Mouse breast cancer cell line derived from C57BL/6; "LG" means lung—these cells were isolated from experimental lung metastasis foci; the cells a express 5-fold higher levels of CCL3 mRNA compared with Met-1) (see FIG. 5)

Figure 6:
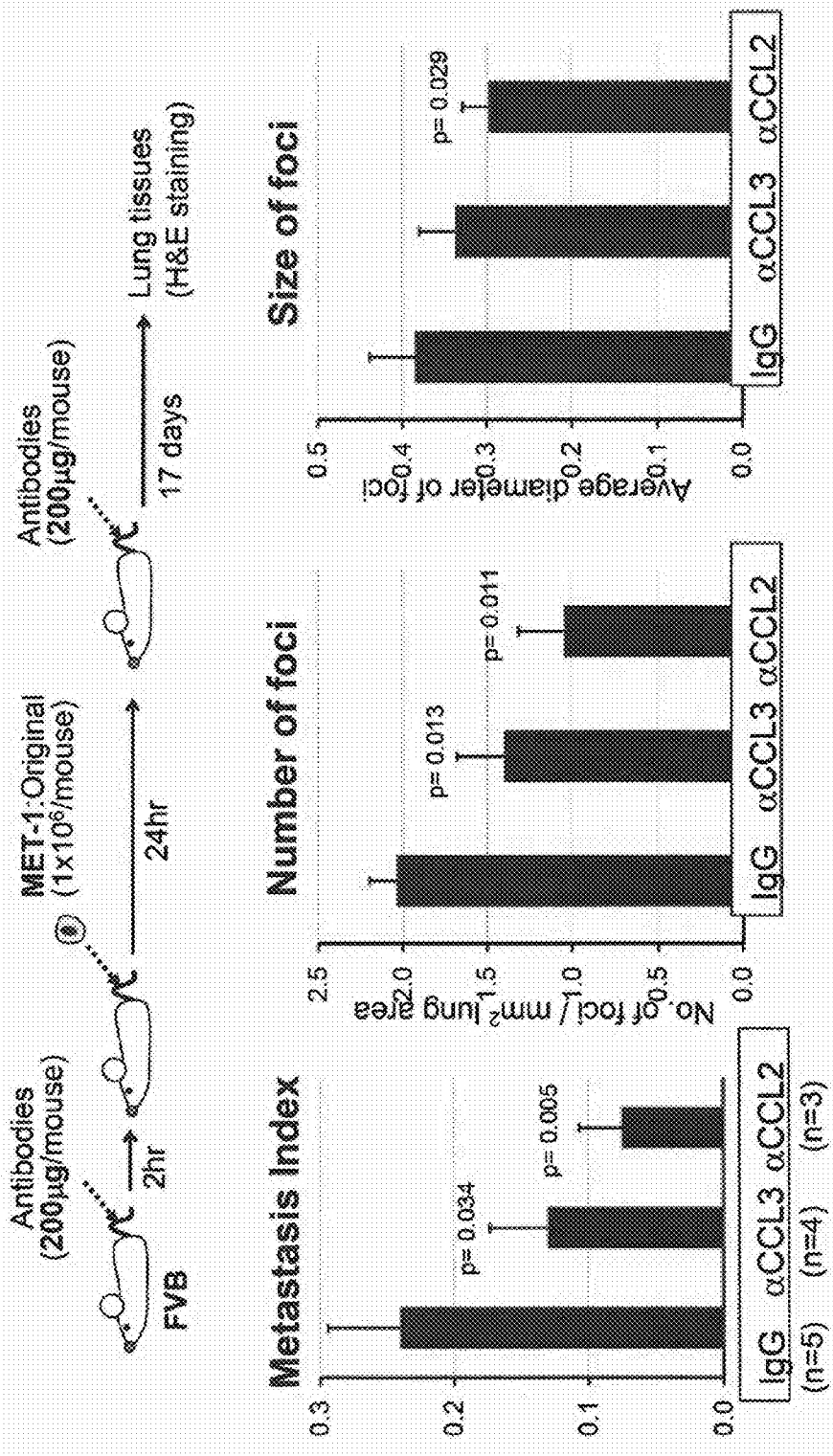
FIG. 6. Neutralizing antibody to CCL3 inhibits metastasis of Met1 cells in an FVB background.
Figure 7:
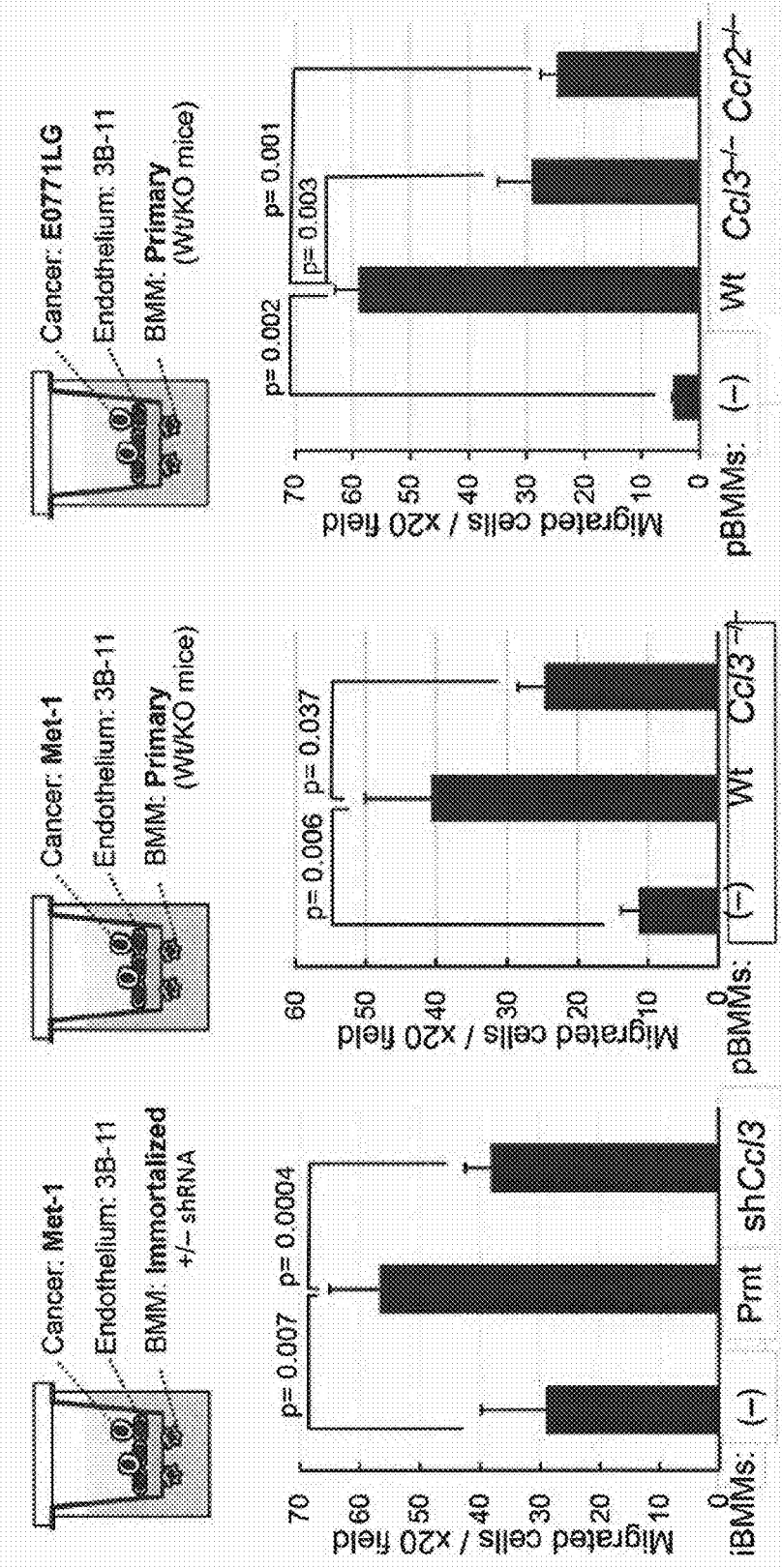
FIG. 7. Macrophage-synthesized CCL3 inhibits transendothelial migration of tumor cells that is a mimic of the extravasation event in vivo.

As shown in FIG. 6, a neutralizing antibody to CCL3 was found to inhibit lung metastasis of Met1 cells in an FVB background. Macrophage-synthesized CCL3 was also found to inhibit transendothelial migration of tumor cells, a mimic of the extravasation event in vivo (FIG. 7). These data support the genetic in vivo model that shows CCL3 stimulates seeding of metastatic tumor cells.

Figure 8:
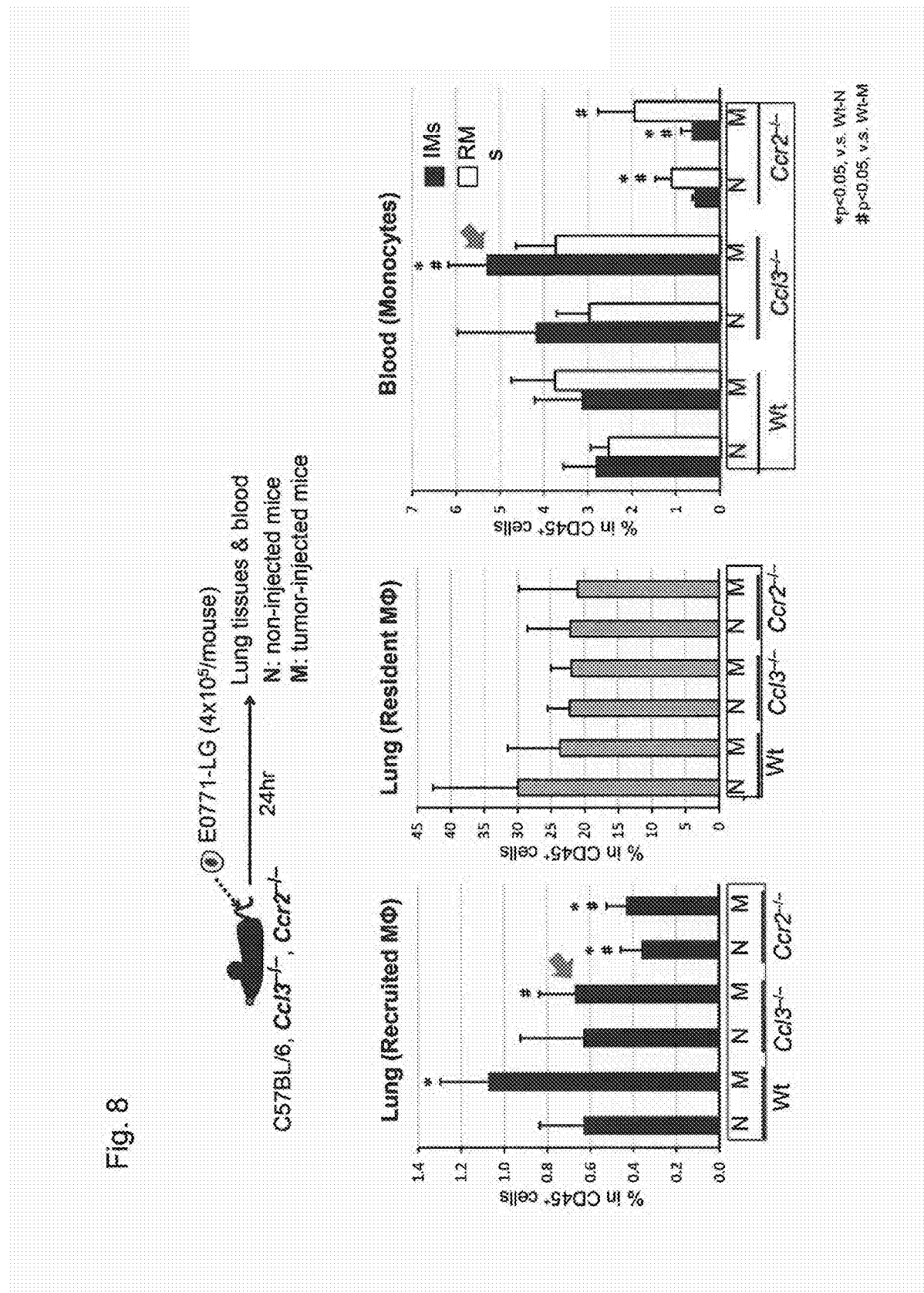
FIG. 8. CCL3 is required for the recruitment of lung monocytes but does not reduce circulating monocytes, unlike CCR2 deficiency.
Figure 9:
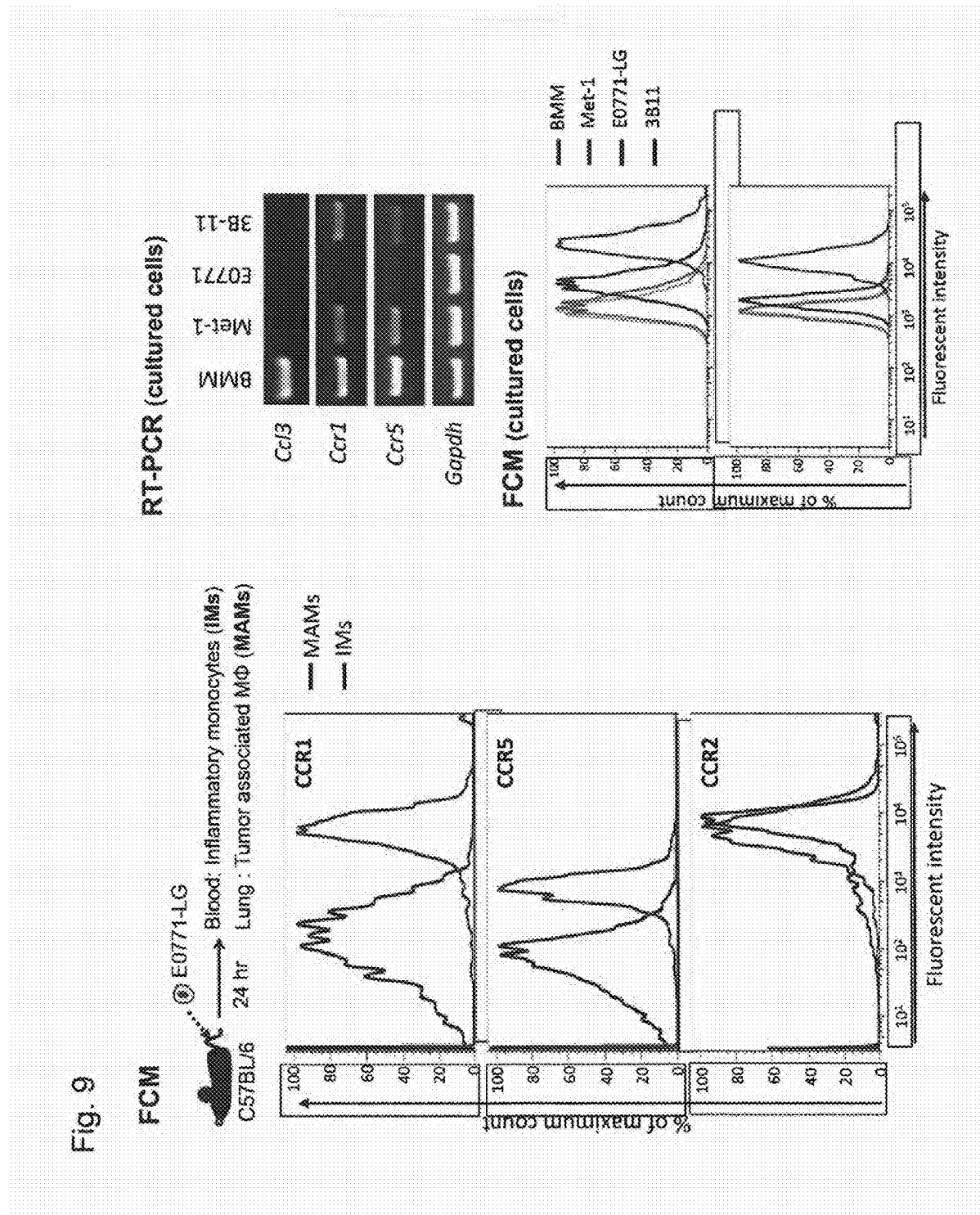
FIG. 9. Expression of the CCL3 receptors CCR1 and CCR5 is increased in recruited macrophages.

It was also observed that CCL3 is required for the recruitment of lung monocytes but does not reduce circulating monocytes, unlike CCR2 deficiency (FIG. 8). It was further determined, as shown in FIG. 9, that expression of the CCL3 receptors CCR1 and CCR5 is increased in recruited macrophages.

Figure 10:
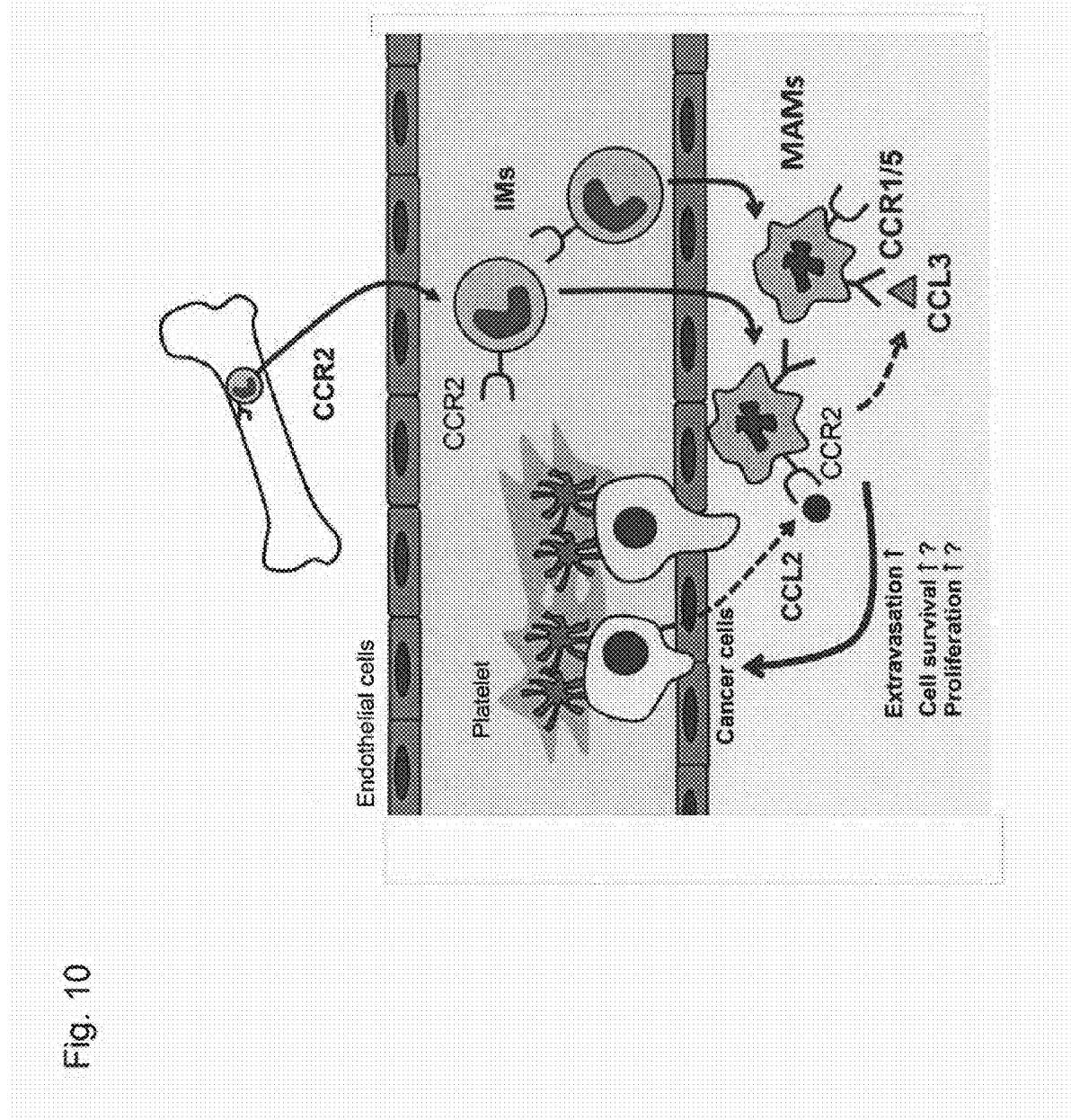
FIG. 10. Model for CCL3 recruitment of monocytes to support the seeding and growth of metastatic tumor cells.

Without being bound by theory, FIG. 10 shows a proposed model for CCL3 recruitment of monocytes to support the seeding and growth of metastatic tumor cells. CCL3 is a valid target to inhibit metastasis. It is apparent that denying trophic support supplied by macrophages to metastatic tumors will reduce the amount of metastasis.

In further studies on the inhibition of CCL3 and spontaneously-arising tumors caused by expression of the Polyoma Middle T oncoprotein (PyMT) using a genetic knockout of CCL3, it was concluded that CCL3 enhances metastasis at the metastatic site. In addition, part of the action of CCL3 in promoting metastasis is via the retention of monocytes in the tissue and the subsequent promotion of differentiation into metastasis-associated macrophages (MAMs). This results in, for example, the enhancement of tumor cell extravasation in the lung.

CCL3 was also found to signal via the receptor CCR1 that is up-regulated on MAMs as they differentiate from monocytes. Accordingly, CCR1 is also a therapeutic target. In this regard, CCL3 to CCR1 signaling is required for MAMs to adhere to tumor cells via an integrin-mediated mechanism. Inhibition of CCL3 or CCR1 inhibits metastasis. CCL3 is also up-regulated in human monocytes/macrophages by CCL2 acting through CCR2. This CCL2 is derived from tumor cells.

These signaling pathways have been validated in two types of mouse mammary cancer cells (Met1 and E0771) and in human MDA-MB 231 cells as well as the PyMT model (not CCR1 deficient).

What is claimed is:

1. A method of inhibiting metastasis in a subject of a primary tumor which requires macrophages for progression, comprising administering to the subject an amount of an inhibitor of CCL3 activation of macrophages effective to inhibit metastasis of a tumor wherein the inhibitor of CCL3 activation of macrophages is a neutralizing antibody or a fragment of such an antibody.

2. The method of claim 1, wherein the tumor is a tumor of the breast, nasopharynx, pharynx, lung, bone, brain, sialaden, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid or skin or is a glioma.

3. The method of claim 1, wherein the tumor is a tumor of the breast, endometrium or prostate or wherein the primary tumor is a brain tumor or glioma.

4. The method of claim 1, wherein metastasis is inhibited in lung, bone and/or brain tissue.

5. The method of claim 1, wherein the antibody is a human antibody, a humanized antibody or a chimeric antibody or wherein the fragment is of a human antibody, of a humanized antibody or of a chimeric antibody.

6. The method of claim 1, wherein the CCL3 is metastasis-associated-macrophage-secreted CCL3.

7. The method of claim 1, further comprising administering to the subject an amount of an antagonist of a CCR5 receptor or an antagonist of a CCR1 receptor.

* * * * *

SEQUENCE LISTING

```
<160> NUMBER OF SEQ ID NOS: 2

<210> SEQ ID NO 1
<211> LENGTH: 92
<212> TYPE: PRT
<213> ORGANISM: Homo sapiens

<400> SEQUENCE: 1

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 2
<211> LENGTH: 355
<212> TYPE: PRT
<213> ORGANISM: Homo sapiens

<400> SEQUENCE: 2
```

```
Met Glu Thr Pro Asn Thr Thr Glu Asp Tyr Asp Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
        50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
            85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
            130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
            165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
            195                 200                 205

Val Leu Pro Leu Leu Val Met Ile Ile Cys Tyr Thr Gly Ile Ile Lys
            210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
            245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
            275                 280                 285

Ile Ala Tyr Thr His Cys Cys Val Asn Pro Val Ile Tyr Ala Phe Val
            290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
            325                 330                 335

Glu Arg Val Ser Ser Thr Ser Pro Ser Thr Gly Glu His Glu Leu Ser
            340                 345                 350

Ala Gly Phe
355
```